United States Patent [19]
Zeghdaoui et al.

[11] Patent Number: 5,849,771
[45] Date of Patent: Dec. 15, 1998

[54] PHOSPHORYLATED NITRONE DERIVATIVES, METHOD FOR PREPARING SAME, AND COMPOSITIONS CONTAINING SAID DERIVATIVES

[75] Inventors: Abdelhamid Zeghdaoui, Commune de Bourouba, Algeria; Jean-Pierre Finet, Raphele les Arles, France; Beatrice Tuccio, Marseilles, France; Viviane Cerri, Le Pradet, France; Paul Tordo, Marseilles, France

[73] Assignee: Centre National de la Recherche Scientifique (C.N.R.S.), Paris, France

[21] Appl. No.: 913,043

[22] PCT Filed: Mar. 6, 1996

[86] PCT No.: PCT/FR96/00353
§ 371 Date: Jan. 26, 1998
§ 102(e) Date: Jan. 26, 1998

[87] PCT Pub. No.: WO96/27601
PCT Pub. Date: Sep. 21, 1996

[30] Foreign Application Priority Data

Mar. 6, 1995 [FR] France .................... 95 02598

[51] Int. Cl.$^6$ .......... A61K 31/44; A61K 31/21
[52] U.S. Cl. .......... 514/357; 514/344; 514/640; 514/824; 546/330; 546/334; 546/335; 546/336; 546/337; 558/87; 558/168; 558/175
[58] Field of Search .................. 546/330, 334, 546/335, 336, 337; 558/87, 168, 175; 514/344, 357, 640, 824

[56] References Cited

FOREIGN PATENT DOCUMENTS

WO 91/05552  5/1991  WIPO .
WO 95/03314  2/1995  WIPO .
WO 95/11908  5/1995  WIPO .

*Primary Examiner*—Peter O'Sullivan
*Attorney, Agent, or Firm*—Young & Thompson

[57] ABSTRACT

Compounds of formula (I), wherein Ar, $R_1$, $R_2$, Y and R are as defined in claim 1, are effective as traps for free radicals.

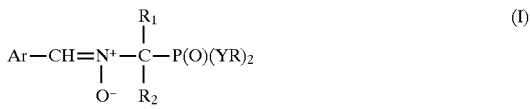

(I)

20 Claims, No Drawings

PHOSPHORYLATED NITRONE DERIVATIVES, METHOD FOR PREPARING SAME, AND COMPOSITIONS CONTAINING SAID DERIVATIVES

The invention relates to phosphorylated nitrone derivatives which can be employed as traps for free radicals.

Because of their physicochemical properties, such compounds are greatly sought after in the fields of cosmetology and of medicine.

It has been demonstrated in particular that, under the action of many intracellular processes, the oxygen conveyed in the body by respiration can be reduced to various reactive oxygen-containing species, prooxidants of the $O_2^{\cdot-}$ type (the superoxide radical), HO$^\cdot$ (the hydroxyl radical) and HOO$^\cdot$ (the perhydroxyl radical).

In a normal situation these species are rapidly removed by reaction with enzymatic or nonenzymatic antioxidant substances such as catalase, superoxide dismutase, glutathione peroxidase, glutathione, vitamin E or ascorbate, with the result that the stationary concentration of reactive oxygen-containing species in the human biological media is very low.

It happens, however, that an imbalance is established between antioxidants and prooxidants, resulting in an abnormal increase in the proportion of prooxidants. This is then spoken of as a situation of oxidative stress.

Such a situation has harmful consequences, since the oxygen-containing free radicals thus generated, which are highly unstable, react quite indiscriminately with a large number of the compounds present in the cell medium, namely proteins, amino acids, carbohydrates, DNA bases and organic acids and especially lipids, which are polyunsaturated fatty acids. The resulting damage entails, for example, the inactivation of many enzymes as well as changes involving the permeability and the fluidity of the cell membranes.

It has been possible to demonstrate that various cardio-vascular pathological states such as coronary ischaemia, arteriosclerosis and infarctus involve an oxidative stress, that is to say an overproduction of radicals of the $O_2^{\cdot-}$, HOO$^\cdot$ and HO$^\cdot$ type. The same applies in the case of many inflammatory or infectious processes or of cell aging.

More than any other organ, the brain is sensitive to this oxidative stress state since the disturbances due to the uncontrolled proliferation of oxygen-containing free radicals result in an irreversible neuronal degeneracy.

Now, the brain is particularly vulnerable, insofar as it contains a high proportion of peroxidizable fatty acids and many regions which are very rich in iron (in the form of ferritin), which, acting as catalyst in the production of the oxygen-containing toxic species, contributes to the worsening of this oxidative stress state. Similarly, the rarity of the antioxidant substances where the brain is concerned cannot but help to facilitate the establishment of the oxidative stress state.

It is consequently understandable that the search for efficient traps for free radicals has developed. As a matter of fact, a simple means of curbing the proliferation of these toxic radicals is to bring them into contact with a substance which is sufficiently reactive to enter into competition with the other cell constituents.

Hitherto, a specific nitrone, α-phenyl-tert-butylnitrone (PBN) has been found particularly effective as an antioxidant exogenous substance capable of reversing the harmful effects of oxygen-containing free radicals, regardless of whether the latter have been generated during a cerebral ischaemia-reperfusion sequence (J. M. Carney et al.; J. of Mol. Neurosc. 1991, 3, 45–57) or following cerebral aging (J. M. Carney et al., Proc. Natl. Acad. Sci. USA, 88, 1991, 3633–3636). However, the low stability of the resulting adducts, obtained by the action of PBN on the various free radicals, has encouraged the present inventors to develop novel molecules which can also be employed as traps for free radicals but which are endowed with better physicochemical properties.

As a result of intensive research they have discovered new phosphorylated nitrones exhibiting a high stability, a good solubility in biological media, a good lipophilicity so as to be able to penetrate the membrane wall, and resulting in the formation of trapping adducts which are comparatively more stable.

The subject-matter of the invention is therefore phosphorylated nitrones of general formula I:

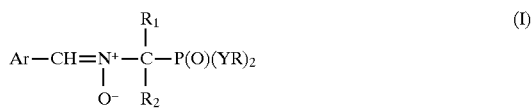

in which $R_1$ and $R_2$ independently are a $C_1$–$C_{18}$ alkyl or a phenyl group optionally substituted by $C_1$–$C_{18}$ alkyl, $C_1$–$C_{18}$ alkoxy or a halogen atom;

Y is O or $CH_2$;

R is a hydrogen atom, a $C_1$–$C_{18}$ alkyl group or a $C_6$–$C_{18}$ aryl group and, when Y is O, R can also denote an alkali metal;

Ar is an aromatic nucleus selected from a phenyl, naphthyl, 2-pyridyl, 3-pyridyl and 4-pyridyl nucleus or a benzopyridyl nucleus of formula (i)

in which one of $X_1$, $X_2$, $X_3$ and $X_4$ is a nitrogen atom, the others being a carbon atom, the endocyclic nitrogen atom of the 2-pyridyl, 3-pyridyl, 4-pyridyl or benzopyridyl nucleus (i) being optionally N-oxidized or substituted by a $C_1$–$C_{18}$ alkyl group or a $C_6$–$C_{18}$ aryl group and, the said aromatic nucleus being optionally C-substituted by one or more halogen atoms or one or more groups selected from $C_1$–$C_{18}$ alkyl, cyano, hydroxyl, $C_1$–$C_{18}$ alkoxy, $C_6$–$C_{18}$ aryloxy, carboxyl, $C_1$–$C_{18}$ alkoxy-carboyl, nitro, trifluoromethyl, —$SO_3M$ where M is an alkali metal or a hydrogen atom, amino optionally alkylated by one or two $C_1$–$C_{18}$ alkyl groups;

and —$N^+R_3R_4R_5$ in which $R_3$, $R_4$ and $R_5$ are selected independently of one another from $C_1$–$C_{18}$ alkyl, it being understood that when the group Ar includes a quaternary nitrogen atom, it additionally includes the physiologically acceptable negative counterion necessary for electrical neutrality;

and their physiologically acceptable salts obtained by the action of an inorganic or organic base or acid.

According to the invention an alkyl group is intended to mean both alkyl groups which are linear and those which are branched.

Similarly, the term alkoxy includes alkoxy radicals in which the alkyl part is linear, as well as those in which the alkyl part is branched.

An example of $C_1$–$C_{18}$ alkyl group which may be mentioned is the methyl, ethyl, propyl, isopropyl, n-butyl, secbutyl, tert-butyl, n-pentyl, neopentyl, hexyl, heptyl, decyl, dodecyl, tridecyl and octadecyl groups.

$C_1$–$C_{18}$ alkoxy group is intended to mean especially the methoxy, ethoxy, n-propoxy, isopropoxy, n-butoxy, sec-butoxy, tert-butoxy, n-pentoxy and neopentoxy groups as well as fatty alcohol-derived alkoxy chains.

Some examples of $C_6$–$C_{18}$ aryl groups are the phenyl, naphthyl, anthryl, 1,2,3,4-dibenzonaphthyl and pyrenyl groups.

Aryloxy is intended to mean an aryl group, as defined above, bonded to an oxygen atom.

The term halogen generally denotes fluorine, chlorine, bromine or iodine. When this halogen substituent is bonded to the aromatic nucleus represented by Ar, it is preferred that it should be a fluorine atom.

According to the invention the expression alkali metal denotes any one of the elements chosen from Li, Na, K, Rb and Cs, sodium and potassium being nevertheless preferred.

When Ar denotes the benzopyridyl radical of formula (i), this radical may be bonded to the sp$_2$ carbon of the compound of formula I via any one of its carbon apexes, regardless of whether this apex belongs to the homocyclic or the heterocyclic ring.

In addition, when Ar includes a quaternary nitrogen, the presence of a negative counterion is necessary to ensure electrical neutrality.

This is especially the case when Ar is a pyridyl nucleus or a benzopyridyl nucleus of formula (i) in which the endocyclic nitrogen atom is alkylated.

This is also the case when the aromatic nucleus represented by Ar is substituted by an —$N^+R_3R_4R_5$ group.

The nature of the counterion is not essential according to the invention, as long as this anion is physiologically acceptable.

Nevertheless, the preferred counterions which may be mentioned are halide, carbonate, sulphonate, sulphate, phosphate, phosphonate and carboxylates such as oxalate, citrate, succinate, maleate or lactate.

It will also be noted that the compounds of formula I in which $R_1$ is other than $R_2$ have at least one asymmetric carbon. In this case the present invention applies not only to the racemate but also to the laevorotatory and dextrorotatory isomers specifically, as well as to the mixtures of the laevorotatory isomer and of the dextrorotatory isomer in any proportion.

The salts of the compounds of formula I form another subject-matter of the invention.

When the compound of formula I includes an acidic functional group, it will be possible to obtain an addition salt with a base. Examples of such salts include salts formed with an alkali metal or an alkaline-earth metal, such as sodium, potassium, calcium or magnesium, and salts formed with an organic base, such as a salt formed with dicyclohexylamine.

When the compound of formula I includes a basic functional group, it will be possible to obtain an addition salt with an acid. Examples of such addition salts with acids include the salts formed with an inorganic acid such as hydrochloric acid, sulphuric acid or phosphoric acid, salts formed with a carboxylic organic acid such as oxalic acid, maleic acid, succinic acid or citric acid, and salts formed with a sulphonic organic acid such as methanesulphonic acid, benzene-sulphonic acid or p-toluenesulphonic acid.

A first group of preferred compounds consists of the compounds of formula I in which Ar is an aromatic nucleus selected from phenyl, 2-pyridyl, 3-pyridyl or 4-pyridyl, optionally N-oxidized, the said aromatic nucleus being optionally C-substituted by a halogen atom, preferably a fluorine atom, or a group selected from $C_1$–$C_{18}$ alkyl, cyano, $C_1$–$C_{18}$ alkoxy, carboxyl, $C_1$–$C_{18}$ alkoxycarbonyl, nitro, trifluoromethyl and —$SO_3M$ where M is an alkali metal and preferably sodium; and —$N^+(R_3)_3$ in which $R_3$ denotes $C_1$–$C_{18}$ alkyl, it being understood that when the group Ar includes a quaternary nitrogen atom, it additionally includes the physiologically acceptable negative counterion necessary for electrical neutrality;

and their physiologically acceptable salts obtained by the action of an inorganic or organic base or acid.

A second group of preferred compounds consists of the compounds of formula I in which Ar is phenyl optionally substituted in an ortho, meta or para position by a halogen atom or a group selected from $C_1$–$C_{18}$ alkyl, nitro, amino, hydroxyl, $C_1$–$C_{18}$ alkoxy and $C_6$–$C_{18}$ aryloxy, and their physiologically acceptable salts obtained by the action of an inorganic or organic base or acid.

A third group of preferred compounds consists of the compounds of formula I in which Ar is an aromatic nucleus selected from 2-pyridyl, 3-pyridyl and 4-pyridyl, the said aromatic nucleus being optionally substituted on the nitrogen atom by a substituent chosen from $C_1$–$C_{18}$ alkyl and $C_6$–$C_{18}$ aryl, and their physiologically acceptable salts obtained by the action of an inorganic or organic base or acid.

A fourth group of preferred compounds consists of the compounds of formula I in which Ar is an aromatic nucleus selected from 2-pyridyl, 3-pyridyl and 4-pyridyl, the said aromatic nucleus being N-oxidized, and their physiologically acceptable salts obtained by the action of an inorganic or organic base or acid.

Among these compounds those in which Y denotes O and $R_1$ and $R_2$ independently are $C_1$–$C_{18}$ alkyl and, better still, $C_1$–$C_5$ alkyl are more particularly preferred.

R advantageously is a $C_1$–$C_{18}$ alkyl group or an alkali metal and more particularly sodium, potassium, lithium or caesium.

The following compounds are more particularly preferred:

diethyl 1-(N-benzylidene-N-oxy)amino-1-methylethylphosphonate;

diethyl 1-[N-oxy-N-[4-(N'-oxypyridyl)formylene]amino]-1-methylethylphosphonate;

diethyl 1-[[N-(4-nitrophenyl)formylene]-N-oxyamino]-1-methylethylphosphonate;

diethyl 1-[[N-(4-chlorophenyl)formylene]-N-oxyamino]-1-methylethylphosphonate; and their physiologically acceptable salts obtained by the action of an inorganic or organic base or acid.

The compounds of the invention can be prepared in a general manner by reaction of a compound of formula II

in which $R_1$, $R_2$, Y and R have the meanings shown above, activated beforehand with a suspension of metallic zinc in an aqueous solution of ammonium chloride, with an aldehyde of formula III

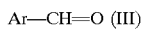

in which Ar is as defined above. The stage of activation of the compound of formula II can be carried out by applying the following stages:

(i) in a first step the compound of formula II above is reacted in an appropriate solvent with metallic zinc in the presence of an aqueous solution of ammonium chloride, for example at a temperature of between −10° C. and the ambient temperature, preferably between −5° C. and the ambient temperature, better still between 0° C. and the ambient temperature.

(ii) the reaction mixture is then filtered. The filtrate obtained, containing the active form of the compound of formula II, can be employed as it is in the process described above, consisting of reacting the activated compound of formula II with a compound of formula III.

A person skilled in the art will have no trouble in determining the appropriate solvent for the activation stage (i). The solvent in question will be preferably characterized by a high polarity, its optional miscibility with water being preferable but not essential. The said solvent is preferably chosen so as to solubilize the nitro derivative of formula II.

As a particularly advantageous example of solvents there will be mentioned organic alcohols of formula T—OH where T is $C_1$–$C_6$ alkyl, preferably $C_1$–$C_4$ alkyl, optionally mono- or polyhydroxylated.

Methanol and preferably ethanol may be mentioned by way of example.

The use of solvent mixtures can also be found highly profitable. It will thus be possible to opt for mixtures of the alcohol/water type and more particularly ethanol/water.

The process described above for the activation of the compound of formula II with zinc in aqueous ammonium chloride medium is given by way of example as a preferred embodiment. However, the invention does not intend to limit the activation process to this particular embodiment.

Reaction of the activated compound of formula II with the compound of formula III is preferably implemented at a temperature of between the ambient temperature and 200° C., better still between the ambient temperature and 150° C. or else between the ambient temperature and 100° C.

A solvent may be added to the reaction mixture, if necessary, during the reaction of the compound III with the activated compound II, this being even assuming that the filtrate collected in stage (ii) of the activation process described above is employed as starting reactant.

Here, too, the determination of the appropriate solvent is within the competence of a person skilled in the art. A polar solvent is again particularly indicated, the abovementioned organic alcohols being particularly advantageous. In general the use of ethanol is recommended.

It will be noted that in the process of preparation of the compounds of formula I the nature of the metallic zinc is not essential.

However, the implementation of the said process can be simplified by the use of zinc powder, optionally activated according to one of the processes well known to an organic chemist.

The present invention also proposes, as an alternative form of the above process, a second synthesis route to the compounds of formula I.

This second process includes the reaction in an appropriate solvent of a compound of formula II

(in which $R_1$, $R_2$, Y and R are as defined above), with a compound of formula III Ar—CH=O (III)

(in which Ar is as defined above),
in the presence of metallic zinc and of acetic acid.

This reaction preferably takes place at a temperature of between −10° C. and the ambient temperature, better still between 0° C. and the ambient temperature.

For optimum efficiency it is clear that this process will be preferably selected in the case of the compounds of formula I in which Ar does not include any functional groups liable to be reduced by the action of metallic zinc in acetic acid. Examples of such functional groups are, for example, the nitro functional group and —N$^+$—O$^-$. In fact, following the reaction of such a compound of formula II with the compound of formula III, an additional stage of oxidation of the said functional group would then be necessary, to end with the desired compound of formula I.

This process is accordingly more particularly recommended for the preparation of the compounds of formula I

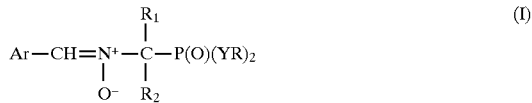

in which
$R_1$ and $R_2$ independently are a $C_1$–$C_{18}$ alkyl or a phenyl group optionally substituted by $C_1$–$C_{18}$ alkyl, $C_1$–$C_{18}$ alkoxy or a halogen atom;
Y is O or $CH_2$;
R is a hydrogen atom, a $C_1$–$C_{18}$ alkyl group or a $C_6$–$C_{18}$ aryl group and, when Y is O, R can also denote an alkali metal;
Ar is an aromatic nucleus selected from a phenyl, naphthyl, 2-pyridyl, 3-pyridyl and 4-pyridyl nucleus or a benzopyridyl nucleus of formula (i)

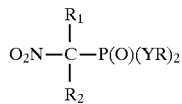

in which one of $X_1$, $X_2$, $X_3$ and $X_4$ is a nitrogen atom, the others denoting a carbon atom,
the said aromatic nucleus being optionally C-substituted by one or more halogen atoms or one or more groups selected from $C_1$–$C_{18}$ alkyl, hydroxyl, $C_1$–$C_{18}$ alkoxy, trifluoromethyl, $C_6$–$C_{18}$ aryl, carboxyl, $C_1$–$C_{18}$ alkoxycarbonyl, —SO$_3$M where M is an alkali metal or a hydrogen atom, amino optionally alkylated by one or two $C_1$–$C_{18}$ alkyl groups, and —N$^+$R$_3$R$_4$R$_5$ in which R$_3$, R$_4$ and R$_5$ are chosen independently of one another from $C_1$–$C_{18}$ alkyl,
it being understood that when the group Ar includes a quaternary nitrogen atom, it additionally includes the physiologically acceptable negative counterion necessary for electrical neutrality;
and their physiologically acceptable salts obtained by the action of an inorganic or organic base or acid.

The compounds of general formula II can be prepared by employing the process described by K. A. Petrov et al. in Zh. Obshch. Khim. 1976, 46, 1226. Other methods which are well known to a person skilled in the art enable these nitrophosphorylated derivatives to be prepared.

As for the compounds of formula III, these are for the most part available commercially and in all cases easily prepared using known methods.

The compounds of the invention are efficient traps for free radicals which can be employed in various fields:
in cosmetology as scavengers for prooxidant species responsible for cell aging;

in therapeutics with a view to reestablishing the equilibrium between prooxidant and antioxidant species, which may have been perturbed, for example following a cerebral aging or during a cerebral ischaemia-reperfusion sequence; the compounds of the invention can also be employed for the treatment of pathological states involving an oxidative stress situation, such as cardiovascular pathological states, for example coronary ischaemia, arteriosclerosis and infarctus; or else further in the field of diagnostics, where they are useful in the evaluation of the oxidative stress.

In actual fact the direct detection of the free radicals $O_2^{\cdot-}$, $HOO^\cdot$ and $HO^\cdot$ which are generated in vivo is not possible by Electron Paramagnetic Resonance (EPR), despite their non-zero spin magnetism, this being because of their instability: these radicals actually have a half-life of the order of $10^{-5}$ to $10^{-3}$ seconds.

For this reason the spin-trapping technique is widely employed for the detection of these radicals.

Its principle is as follows: the biological medium to be tested is placed in the presence of a free-radical trap T. If free radicals such as $O_2^{\cdot-}$, $HO^\cdot$ or $HOO^\cdot$ are present in the medium, they combine with the trap T to form an adduct $(T-O_2)^{\cdot-}$, $(T-OH)^\cdot$ or $(T-OOH)^\cdot$. This adduct is persistently paramagnetic and can therefore be detected by Electron Paramagnetic Resonance (EPR).

Now, with regard to free radicals, the compounds according to the invention have been found to be efficient traps permitting the detection by EPR of the prooxidant free radicals in biological media, especially because of the excellent stability of the trapping adduct formed and of the excellent kinetics of trapping characterizing the compounds of the invention.

When compared with x-phenyl-tert-butylnitrone (PBN) of the state of the art, the compounds of the invention have a better selectivity for the oxygen-containing radical substances. More particularly they permit the detection of the radical $O_2^{\cdot-}$, a detection which cannot be carried out using PBN.

The use of the compounds of the invention is all the more advantageous, since they are soluble in biological media while being capable of entering the intracellular space. It is thought, in fact, that the intracellular radical processes predominate in vivo. It will be noted that by modifying the nature of the group Ar it is possible to modulate the lipophilicity of the nitrone which is synthesized.

Another subject-matter of the invention is a cosmetic or pharmaceutical composition including as active ingredient at least one compound of the invention in combination with an appropriate carrier.

When the compositions of the invention are in solid form, the compounds of the invention are used in combination with various excipients, flavours, dyes, perfumes, lubricants, taste-correctors and organic or inorganic UV screening agents, or more generally fillers such as lactose, starch, sucrose, glucose, sorbitol, crystalline cellulose and silicon dioxide.

Examples of binders which may be mentioned are poly (vinyl alcohol), poly(vinyl ether), ethylcellulose, methylcellulose, acacia, gum tragacanth, gelatin, shellac, hydroxypropylcellulose, dextrin, pectin, ethanol, propanol and water.

The dye may be any one of those appropriate to a cosmetic or therapeutic use.

Examples of taste-correctors include cocoa, mint, borneol and cinnamon.

Examples of excipients which will be mentioned are vegetable or mineral oils, vegetable or mineral waxes, silicones, fatty alcohols and acids, surface-active agents (such as sorbitol esters and their polyoxyethylenated derivatives, polyoxyethylenated castor oils (hydrogenated or otherwise), ethylene oxide/propylene oxide block copolymers, polyoxyethylenated fatty alcohols and sterols, sodium lauryl sulphate, sodium dioctylsulphosuccinate, egg or soya lecithins and polyoxyethylenated silicone oils, protein derivatives, inorganic or organic gelling agents, lanolin and its derivatives and, more generally, plant extracts.

In order to obtain tablets, granules, powders, capsules, gels, creams or ointments, the mixture thus formed is processed in a known manner.

When the compositions of the invention are in the form of liquid or suspension, the nature of the associated carriers varies. It will be possible, for example, to employ water, ethyl alcohol, propylene glycol or isostearyl alcohol. It will also be possible to add preserving agents such as esters of 4-hydroxybenzoic acid.

The quantity of active ingredient which must be added to the composition varies according to whether the said composition is intended for a cosmetological or therapeutic use.

Another subject-matter of the invention is a diagnostic composition which can be employed in the evaluation of the oxidative stress, including at least one compound according to the invention.

The following examples illustrate the invention without any limitation being implied. In the nuclear magnetic resonance (NMR) data the chemical shifts δ are expressed in ppm relative to TMS.

EXAMPLE 1:

Diethyl 1-(N-benzylidene-N-oxy)amino-1-methylethyl-phosphonate

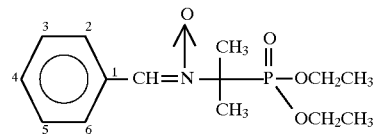

Glacial acetic acid (60 mmol, 3.79 g) is added dropwise to a vigorously stirred mixture of benzaldehyde (10 mmol), of diethyl 1-methyl-1-nitroethylphosphonate (prepared according to the process described in K. A. Petrov, V. A. Chanzov, L. V. Pastukhova and N. N. Bogdanov, *Zh. Obshch. Khim.*, 1976, 46, 1226), (20 mmol, 4.5 g) and of zinc powder (30 mmol, 1.96 g) in 75 ml of 95% ethanol. During the addition the temperature is maintained at 0° C. The mixture is then allowed to return to the ambient temperature and is stirred for 2 to 4 h. The reaction mixture is next left overnight in the refrigerator. After filtration and evaporation of the ethanol at reduced pressure, a residue is obtained which is taken up in ether (50 ml) and extracted with a 1N aqueous solution of $NaHCO_3$ and then with 50 ml of water. The aqueous phase is reextracted and the combined organic phases are dried over anhydrous sodium sulphate. After concentration the residue is taken up in a minimum quantity of dichloromethane and chromatographed three times on a preparative plate of silica 60 (eluent: $CH_2Cl_2$-THF-pentane, 1:1:2 by volume) p Yield: 20%

The expected diethyl 1-(N-benzylidene-N-oxy)amino-1-methylethylphosphonate, isolated in the form of oil, is characterized by the following spectroscopic data:

IR $v_{max}$ (film) /cm$^{-1}$: 1577 (C=N), 1245 (P=O), 1193 (N—O) and 1163 (P—O—C);

$^1$H-NMR (400 MHz) (CDCl$_3$): δ 1.22 (6H, dt, J$_{HH}$ 7.6 and J$_{HP}$ 0.54, OCH$_2$—C$\underline{H}_3$), 1.72 (6H, d, J$_{HP}$ 14.89, C$\underline{Me}_2$), 4.09 (4H, dq, J$_{HH}$ 7.6 and J$_{HP}$ 7.1, O—$\underline{CH}_2$—CH$_3$), 7.28 (2H, m, H$_{3,5}$), 7.29 (1H, m, H$_4$), 7.64 (1H, d, J$_{HP}$ 2.7, C$\underline{H}$=N), 8.17 (2H, dd, J 7.6 and 3.4, H$_{2,6}$);

$^{13}$C-NMR (100.6 MHz) (CDCl$_3$): δ 16.225 (d, J$_{CP}$ 5.7, O—CH$_2$—$\underline{C}$H$_3$), 23.093 (s, C$\underline{Me}_2$), 63.188 (d, J$_{CP}$ 7, O—$\underline{C}$H$_2$—CH$_3$), 72.704 (d, J$_{CP}$ 153.7, $\underline{C}$Me$_2$), 128.210 (s, C$_4$) 128.800 (s, C$_{3,5}$), 130.240 (s, C$_{2,6}$), 130.450 (s, C$_1$), 133.005 (d, J$_{CP}$ 5, $\underline{C}$H=N);

$^{31}$P-NMR (40.5 MHz) (CDCl$_3$): δ 22.222 Analysis: C$_{14}$H$_{22}$NO$_4$P•H$_2$O calculated: C: 52.99, H: 7.62, N: 4.41%
found: C: 52.84, H: 7.63, N: 4.22%

EXAMPLE 2

Diethyl 1-[N-oxy-N-[4-(N'-oxypyridyl)formylene]amino]-1-methylethylphosphonate

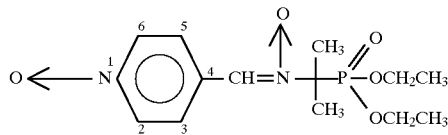

2.5 g of zinc powder are added in small portions over 2 h to a vigorously stirred mixture of 2.25 g (10 mmol) of diethyl 1-methyl-1-nitroethylphosphonate, 10 ml of ethanol, 30 ml of water and 10 ml of a 2N aqueous solution of ammonium chloride cooled to 0°–100° C. The mixture is then allowed to return to the ambient temperature and is stirred for 4 h. After filtration a solution of 1 g (~6 mmol) of 1-[4-(N-oxypyridyl)]formaldehyde in ethanol is added. The reaction mixture is stirred at 40°–50° C. for 6 hours. After concentration of the ethanol at reduced pressure, the residue is taken up in chloroform (50 ml) and extracted with a 1N aqueous solution of NaHCO$_3$ and then with 50 ml of water. The aqueous phase is reextracted and the combined organic phases are dried over sodium sulphate. After concentration the product obtained is purified either by chromatography or on a preparative plate of silica 60 (eluent: CH$_2$Cl$_2$-THF-pentane, 1:1:2 by volume) or by crystallization (dichloromethane-pentane, 1:4).

Yield: 27%.

The expected product has a melting point of between 114° and 115° C. and is characterized by the following spectroscopic data:

IR v$_{max}$ (CCl$_4$) /cm$^{-1}$: 1569 (C=N), 1241 (P=O), 1164 (N—O) and 1052 (P—O—C);

$^1$H-NMR (400 MHz) (CDCl$_3$): δ 1.29 (6H, dt, J$_{HP}$ 7.05 and J$_{HP}$ 0.5, OCH$_2$-C$\underline{H}_3$), 1.77 (6H, d, J$_{HP}$ 14.69, C$\underline{Me}_2$), 4.15 (4H, dq, J$_{HH}$ 7.1 and J$_{HP}$, 8, O—$\underline{CH}_2$—CH$_3$), 7.74 (1H, d, J$_{HP}$ 2.7, C$\underline{H}$=N), 8.12 (4H, s, Ar—H);

$^{13}$C-NMR (100.6 MHz) (CDCl$_3$): δ 16.452 (d, J$_{CP}$ 5.7, O—CH$_2$—$\underline{C}$H$_3$), 23.147 (s, C$\underline{Me}_2$), 63.653 (d, J$_{CP}$ 7, O—$\underline{C}$H$_2$—CH$_3$), 73.779 (d, J$_{CP}$ 152.2, $\underline{C}$Me$_2$), 124.690 (s, C$_{3,5}$), 127.720 (s, C$_4$), 129.670 (d, J$_{CP}$ 4, $\underline{C}$H=N), 139.010 (s, C$_{2,6}$);

$^{31}$P—NMR (40.5 MHz) CDCl$_3$): δ21.474 Analysis: C$_{13}$H$_{21}$N$_2$O$_5$P•H$_2$O calculated: C: 46.71, H: 6.93, N: 8.38%
found: C: 46.83, H: 6.55, N: 8.49%

EXAMPLE 3

Diethyl 1-[[N-(4-nitrophenyl)formylene]-N-oxyamino]-1-methylethylphosphonate

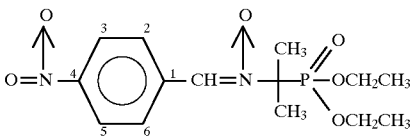

By employing the experimental procedure of Example 2 and by starting with diethyl 1-methyl-1-nitroethylphosphonate and 4-nitrobenzaldehyde, the expected product is isolated in the form of a solid which has a melting point of between 135° and 136° C.

The spectrometry data characterizing this compound are the following:

IR v$_{max}$ (film)/cm$^{-1}$: 1545 (C=N), 1484 (NO$_2$), 1247 (P=O), 1176 (N→O) and 1150 (P—O—C);

$^1$H-NMR (400 MHz) (CDCl$_3$): δ 1.30 (6H, dt, J$_{HH}$ and J$_{HP}$ 3.3, OCH$_2$—C$\underline{H}_3$), 1.82 (6H, d, J$_{HP}$ 14.71, C$\underline{Me}_2$), 4.15 (4H, dq, J$_{HH}$ 7 and J$_{HP}$ 7.6, O—$\underline{CH}_2$—CH$_3$), 7.88 (1H, d, J$_{HP}$ 2.7, C$\underline{H}$=N), 8.21 (2H, d, J$_{HH}$ 9, H$_{3,5}$), 8.39 (2H, d, J$_{HH}$ 9, H$_{2,6}$);

$^{13}$C-NMR (100.6 MHz) (CDCl$_3$): δ 16.476 (d, J$_{CP}$ 5.3, O—CH$_2$—$\underline{C}$H$_3$), 23.276 (s, C$\underline{Me}_2$), 63.664 (d, J$_{CP}$ 6.4, O—$\underline{C}$H$_2$—CH$_3$), 74.059 (d, J$_{CP}$ 152.9, $\underline{C}$Me$_2$), 123.780 (s, C$_{2,5}$), 129.260 (s, C$_{2,6}$), 131.510 (d, J$_{CP}$ 4, $\underline{C}$H=N), 136.310 (s, C$_1$), 147.830 (s, C$_4$);

$^{31}$P-NMR (40.5 MHz) (CDCl$_3$): δ 21.5 Analysis: C$_{14}$H$_{21}$N$_2$O$_5$P•H$_2$O calculated: C: 48.84, H: 6.15, N: 8.14%
found: C: 48.76, H: 6.05, N: 8.29%

EXAMPLE 4

Diethyl 1-[[N-(4-chlorophenyl)formylene]-N-oxyamino]-1-methylethylphosphonate

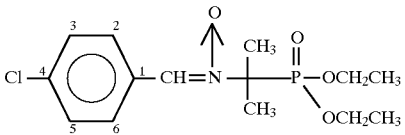

By employing the experimental procedure of Example 2 and by starting with diethyl 1-methyl-1-nitroethylphosphonate and 4-chlorobenzaldehyde the expected product is isolated.

M.p. 80°–81° C.

IR v$_{max}$ (KBr) cm$^{-1}$: 1570 (C=N), 1242 (P=O), 1177 (N→O), 1157 (P—O—C) and 1125 (Cl—C);

$^1$H-NMR (400 MHz, CDCl$_3$): δ 1.26 (6H, t, J$_{HH}$ 7.1, O—CH$_2$—C$\underline{H}_3$), 1.76 (6H, d, J$_{HP}$ 14.83, C$\underline{Me}_2$), 4.13 (4H, dq, J$_{HH}$ 7.1 and J$_{HP}$ 7, O—$\underline{CH}_2$—CH$_3$), 7.30 (2H, d, AB, J 8.7, H$_{3,5}$), 7.68 (1H, d, J$_{HP}$ 2.7, C$\underline{H}$=N), 8.18 (2H, d, AB, J 8.5, H$_{2,6}$);

$^{13}$C-NMR (100.6 MHz, CDCl$_3$): δ 16.420 (d, J$_{CP}$ 5.9, O—CH$_2$—$\underline{C}$H$_3$), 23.226 (s, C$\underline{Me}_2$), 63.390 (d, J$_{CP}$ 7.3, O—$\underline{C}$H$_2$—CH$_3$), 72.9 (d, J$_{CP}$ 153, $\underline{C}$Me$_2$), 128.650 (s, C$_{3,5}$), 129.160 (s, C$_1$), 130.130 (s, C$_{2,6}$), 132.125 (d, J$_{CP}$ 5, $\underline{C}$H=N), 135.750 (s, C$_4$);

$^{31}$P-NMR (40.5 MHz, CDCl$_3$): δ 21.98 C$_{14}$H$_{21}$ClNO$_4$P (M=333.75):

calculated: C: 50.38, H: 6.34, N: 4.20, Cl: 10.60%
found: C: 50.31, H: 6.24, N: 4.14, Cl: 10.60%

EXAMPLE 5

The compounds 5.1, 5.2 and 5.3 reported in the following table are obtained by employing the experimental procedure of Example 2 and by starting with the appropriate reactants of formula II and III.

| Compound | 5.1 | 5.2 | 5.3 |
|---|---|---|---|
| Ar | ⟨phenyl⟩ | ⟨pyridyl-N⟩ | ⟨pyrazinyl⟩ |

EXAMPLE 6

This example illustrates the influence of the group Ar using the lipophilicity of the corresponding nitrone. The partition coefficients $K_p$ of the compounds of Examples 1, 2 and 4 were determined in a two-phase n-octanol/phosphate buffer mixture by UV spectrometric analysis, employing the method described by Konorev et al. in Free Rad. Biol. Med. 14 (1993) 127. The partition coefficients are defined simply as the ratio of the nitrone concentration in the lipophilic phase (n-octanol) to the nitrone concentration in the aqueous phase.

0.25M solutions in 1-octanol of the nitrones of Examples 1, 2 and 4 were prepared and the nitrone concentration was measured at maximum absorption by employing a Unicam UV4 UV/visible spectrometer. The absorption maxima are, respectively:

$\lambda_{max}$=299 nm for the nitrone of Example 1

$\lambda_{max}$=332 nm for the nitrone of Example 2

$\lambda_{max}$=272 nm for the nitrone of Example 4

Identical volumes (2 cm$^3$) of the octanolic nitrone solution prepared above and of a 10 mM phosphate buffer of pH=7.4 are agitated vigorously at 37° C. for 1 hour and the two phases are then separated by centrifuging (1000 g for 20 s) . The respective nitrone concentrations in each phase are then measured.

The results obtained are summarized in Table 2 which follows:

TABLE 2

| Compound | Partition coefficient |
|---|---|
| Ex. 1 | 10.1 ± 0.5 |
| Ex. 2 | 195 ± 10 |
| Ex. 4 | 0.18 ± 0.02 |

From these measurements it follows that the nitrones of Examples 1 and 2 are lipophilic, whereas the nitrone of Example 4 is hydrophilic.

A modulation of the lipophilic properties of the nitrones of the invention is therefore possible by simply modifying the group Ar.

EXAMPLE 7

In this example the electron paramagnetic resonance (EPR) spectra derived from the nitrone of Example 1 (denoted by PPN in the following) after trapping of the radicals HO· and O$_2$·$^-$/HOO· are discussed.

In this experiment the HO· radicals were produced by Fenton's method in a 1.1M phosphate buffer at pH=7 in the presence of the H$_2$O -FeSO$_4$ system. This classical reaction for producing HO· radicals can be expressed more simply as follows:

$H_2O_2 + Fe(II) \rightarrow HO^\cdot + HO^- + Fe(III)$.

FeSO$_4$ (2 mmol dm$^{-3}$) and H$_2$O$_2$ (2 mmol dm$^{-3}$) are added to a solution of a 0.1M phosphate buffer containing 0.1 mol dm$^{-3}$ of the nitrone of Example 1. The EPR spectrum of the adduct from trapping is recorded approximately 40 s after addition of the ferrous sulphate.

For the production of the HOO· radicals the hypoxanthine/xanthine oxidase system is employed in a 0.1M phosphate buffer maintained at ambient temperature. The oxygen resulting in the formation of the HOO· radicals is that initially dissolved in the 0.1M phosphate buffer.

The hypoxanthine/xanthine oxidase system contains 0.1M of a phosphate buffer, 0.4M of hypoxanthine, 1 mM of diethylenetriaminepentaacetic acid (DTPA), 0.4 units cm$^{-3}$ of xanthine oxidase (marketed by the company Boehringer Mannheim Biochemica Co.), and 0.1M of the nitrone being tested. The EPR spectra of the adducts from trapping are recorded approximately 40 s after the addition of xanthine oxidase.

The EPR spectrum of the mixture reveals the formation of the adducts from trapping PPN—OH and PPN—O$_2$H, the formulae of which are respectively

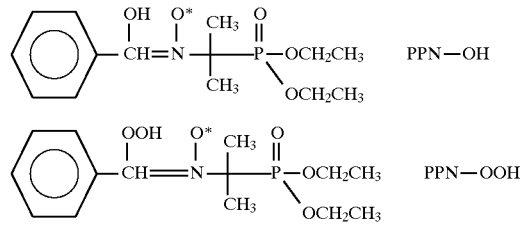

The stability of these adducts makes it possible to measure the respective coupling constants of the unpaired electron with the nuclei of nitrogen ($A_N$), of hydrogen β to the nitrogen atom ($A_H$) and of phosphorus ($A_P$). These values have been shown together in Table 3 which follows:

TABLE 3

| | PPN—OH | PPN—OOH |
|---|---|---|
| $A_N$ | 2.7 G | 2.1 G |
| $A_H$ | 14.6 G | 13.5 G |
| $A_P$ | 43.2 G | 41.3 G |

Note:
G Landé factor

The same experiment was carried out in identical conditions starting with α-phenyl-tert-butylnitrone (PBN), described in the state of the art. No signal could be detected using EPR.

The advantage of the nitrones of the invention over the compounds of the prior art is clear: not only are the adducts from trapping more stable, but also an EPR analysis makes it possible to distinguish the adduct PPN—OH from the adduct PPN—OOH.

EXAMPLE 8

This example reports the results of a kinetic study of the decomposition of the adducts resulting from the trapping of the radical HOO starting with the nitrones of Examples 1, 2 and 4 of the invention, and from the free-radical traps of the prior art, namely PPB (α-phenyl-tert-butylnitrone), POBN (α-(1-oxydopyridin-1-ium-4-yl)-N-tert-butylnitrone and DMPO (5,5-dimethylpyrroline N-oxide).

Decrease in a phosphate buffer medium

The adducts from trapping with the superoxide radical were produced using the riboflavin-DTPA (diethylenetriaminepentaacetic acid) system.

This system contains 1M of DTPA, 0.25M of riboflavin and 0.1M of nitrone in a 0.1M phosphate buffer at pH=5.8.

This mixture is transferred into the cell of a Varian E-9 spectrometer. The cell is then irradiated to generate the superoxide radical in situ. At the end of irradiation the decrease in the adducts (nitrone-OOH) is studied using EPR analysis.

The results of the measurements are reported in the following table in the case of the nitrones of Examples 1 and 2 of the invention, of POBN and of DMPO. In each case the kinetics of disappearance of the adducts are of the first order.

TABLE 4

| Nitrone | Kinetic constant k ($10^3$ s$^{-1}$) | Half-life time (s) |
| --- | --- | --- |
| Example 1 | 2.26 ± 0.03 | 307 |
| Example 2 | 1.63 ± 0.02 | 425 |
| POBN | 37 ± 2 | 19 |
| DMPO | 10.3 ± 0.3 | 67 |

It was observed that the adducts derived from the nitrones of Examples 1 and 2 of the invention degrade approximately 20 times less quickly than the POBN—OOH adducts.

Similarly, the adducts of the invention degrade much more slowly than the DMPO—OOH adduct in the same conditions.

Decrease in an organic medium

The adducts from trapping with the superoxide radical were produced using the lumiflavin-DTPA system in pyridine, or dimethylformamide. This contains 1M of DTPA, 0.25M of lumiflavin and 0.1M of nitrone in pyridine or dimethylformamide.

The operating procedure followed for the study of the decrease of the adduct from trapping is the same as above.

The results obtained are summarized in Table 5.

TABLE 5

| Nitrone | Solvent | k ($10^3$ s$^{-1}$) | Half-life time (s) |
| --- | --- | --- | --- |
| Example 1 | DMF | 0.836 ± 0.001 | 829 |
|  | pyridine | 0.608 ± 0.002 | 1140 |
| Example 2 | DMF | 0.714 ± 0.007 | 971 |
|  | pyridine | 0.549 ± 0.003 | 1263 |
| Example 4 | DMF | 0.761 ± 0.003 | 911 |
|  | pyridine | 0.573 ± 0.001 | 1210 |
| PBN | DMF | 2.76 ± 0.04 | 251 |
|  | pyridine | 2.62 ± 0.14 | 265 |
| POBN | DMF | 2.29 ± 0.02 | 303 |
|  | pyridine | 2.21 ± 0.19 | 314 |
| DMPO | DMF | 1.53 ± 0.02 | 453 |
|  | pyridine | 1.36 ± 0.02 | 510 |

From Table 5 it follows that the adducts derived from nitrones of Examples 1, 2 and 4 are degraded approximately three times more slowly than the POBN—OOH and PBN—OOH adducts.

Similarly, the adducts of the invention are degraded much more slowly than the DMPO-OOH adduct.

In contrast to the acyclic nitrones available in the prior art, the nitrones of the invention are efficient traps for the superoxide radical not only in organic media but also in aqueous media. The compounds of the invention in particular produce stable adducts which give rise to intense signals in EPR.

The nitrones of the invention also permit the trapping of various carbon-containing radicals such as $CH_3\cdot$, $HOCH_2\cdot$, $HO(CH_3)CH\cdot$ and $HOOC\cdot$.

We claim:

1. Compounds of general formula I:

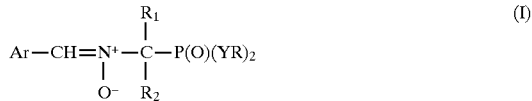

in which $R_1$ and $R_2$ independently are a $C_1$–$C_{18}$ group or a phenyl group optionally substituted by $C_1$–$C_{18}$ alkyl, $C_1$–$C_{18}$ alkoxy or a halogen atom;

Y is O or $CH_2$;

R is a hydrogen atom, a $C_1$–$C_{18}$ alkyl group or a $C_6$–$C_{18}$ aryl group and, when Y is O, R can also be an alkali metal;

Ar is an aromatic nucleus selected from a phenyl, naphthyl, 2-pyridyl, 3-pyridyl and 4-pyridyl nucleus or a benzopyridyl nucleus of formula (i)

in which one of $X_1$, $X_2$, $X_3$ and $X_4$ is a nitrogen atom, the others being a carbon atom, the endocyclic nitrogen atom of the 2-pyridyl, 3-pyridyl, 4-pyridyl or benzopyridyl nucleus (i) being optionally N-oxidized or substituted by a $C_1$–$C_{18}$ alkyl group or a $C_6$–$C_{18}$ aryl group and, the said aromatic nucleus being optionally C-substituted by one or more halogen atoms or one or more groups selected from $C_1$–$C_{18}$ alkyl, cyano, hydroxyl, $C_1$–$C_{18}$ alkoxy, $C_6$–$C_{18}$ aryloxy, carboxyl, $C_1$–$C_{18}$ alkoxy-carbonyl, nitro, trifluoromethyl, —$SO_3M$ where M is an alkali metal or a hydrogen atom, amino optionally alkylated by one or two $C_1$–$C_{18}$ alkyl groups; and —$N^+R_3R_4R_5$, in which $R_3$, $R_4$ and $R_5$ are selected independently of one another from $C_1$–$C_{18}$ alkyl, it being understood that when the group Ar includes a quaternary nitrogen atom, it additionally includes the physiologically acceptable negative counterion necessary for electrical neutrality;

and their physiologically acceptable salts obtained by the action of an inorganic or organic base or acid.

2. Compounds according to claim 1 of formula I in which Ar is an aromatic nucleus selected from phenyl, 2-pyridyl, 3-pyridyl or 4-pyridyl, optionally N-oxidized, the said aromatic nucleus being optionally C-substituted by a halogen atom, or a group selected from $C_1$–$C_{18}$ alkyl, cyano, $C_1$–$C_{18}$ alkoxy, carboxyl, $C_1$–$C_{18}$ alkoxycarbonyl, nitro, trifluoromethyl and —$SO_3M$ where M is an alkali metal and and —$N^+(R_3)_3$ in which $R_3$ is $C_1$–$C_{18}$ alkyl, it being understood that when the group Ar includes a quaternary nitrogen atom, it additionally includes the physiologically acceptable negative counterion necessary for electrical neutrality;

and their physiologically acceptable salts obtained by the action of an inorganic or organic base or acid.

3. Compounds according to claim 1, wherein Ar is phenyl optionally substituted in an ortho, meta or para position by a halogen atom or a group selected from $C_1$–$C_{18}$ alkyl, nitro, amino, hydroxyl, $C_1$–$C_{18}$ alkoxy and $C_6$–$C_{18}$ aryloxy, and their physiologically acceptable salts obtained by the action of an inorganic or organic base or acid.

4. Compounds according to claim 1, wherein Ar is an aromatic nucleus selected from 2-pyridyl, 3-pyridyl and 4-pyridyl, the said aromatic nucleus being optionally substituted on the nitrogen atom by a substituent selected from $C_1$–$C_{18}$ alkyl and $C_6$–$C_{18}$ aryl, and their physiologically acceptable salts obtained by the action of an inorganic or organic base or acid.

5. Compounds according to claim 1, wherein Ar is an aromatic nucleus selected from 2-pyridyl, 3-pyridyl and 4-pyridyl, the said aromatic nucleus being N-oxidized, and their physiologically acceptable salts obtained by the action of an inorganic or organic base or acid.

6. Compounds according to claim 1, of formula I in which $R_1$ and $R_2$ independently are $C_1$–$C_{18}$ alkyl and Y is O, and their physiologically acceptable salts obtained by the action of an inorganic or organic base or acid.

7. Compounds according to claim 1, of formula I in which, when Ar includes a quaternary nitrogen atom, the counterion is selected from a halide, a carbonate, a sulphonate, a sulphate, a phosphate, a phosphonate and a carboxylate.

8. Compounds according to claim 1, selected from:
diethyl 1-(N-benzylidene-N-oxy)amino-1-methylethylphosphonate;
diethyl 1-[N-oxy-N-[4-(N'-oxypyridyl)formylene]amino]-1-methylethylphosphonate;
diethyl 1-[[N-(4-nitrophenyl)formylene]-N-oxyamino]-1-methylethylphosphonate;
diethyl 1-[[N-(4-chlorophenyl)formylene]-N-oxyamino]-1-methylethylphosphonate; and
their physiologically acceptable salts obtained by the action of an inorganic or organic base or acid.

9. Process for the preparation of the compounds of general formula I

in which $R_1$ and $R_2$ independently are a $C_1$–$C_{18}$ alkyl or a phenyl group optionally substituted by $C_1$–$C_{18}$ alkyl, $C_1$–$C_{18}$ alkoxy or a halogen atom;

Y is O or $CH_2$;

R is a hydrogen atom, a $C_1$–$C_{18}$ alkyl group or a $C_6$–$C_{18}$ aryl group and, when Y is O, R can also be an alkali metal;

Ar is an aromatic nucleus selected from a phenyl, naphthyl, 2-pyridyl, 3-pyridyl and 4-pyridyl nucleus or a benzopyridyl nucleus of formula (i)

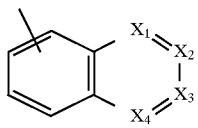

in which one of $X_1$, $X_2$, $X_3$ and $X_4$ is a nitrogen atom, the others being a carbon atom, the endocyclic nitrogen atom of the 2-pyridyl, 3-pyridyl, 4-pyridyl or benzopyridyl nucleus (i) being optionally N-oxidized or substituted by a $C_1$–$C_{18}$ alkyl group or a $C_6$–$C_{18}$ aryl group and, the said aromatic nucleus being optionally C-substituted by one or more halogen atoms or one or more groups selected from $C_1$–$C_{18}$ alkyl, cyano, hydroxyl, $C_1$–$C_{18}$ alkoxy, $C_6$–$C_{18}$ aryloxy, carboxyl, $C_1$–$C_{18}$ alkoxy-carbonyl, nitro, trifluoromethyl, —$SO_3M$ where M is an alkali metal or a hydrogen atom, amino optionally alkylated by one or two $C_1$–$C_{18}$ alkyl groups;

and —$N^+R_3R_4R_5$ in which $R_3$, $R_4$ and $R_5$ are selected independently of one another from $C_1$–$C_{18}$ alkyl, it being understood that when the group Ar includes a quaternary nitrogen atom, it additionally includes the physiologically acceptable negative counterion necessary for electrical neutrality;

and their physiologically acceptable salts obtained by the action of an inorganic or organic base or acid wherein a compound of formula II:

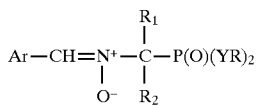

(in which $R_1$, $R_2$, Y and R are as defined above), activated beforehand with a suspension of metallic zinc in an aqueous solution of ammonium chloride, is reacted in an appropriate solvent with an aldehyde of formula III:

$$Ar\text{—}CH\text{=}O \quad (III)$$

(in which Ar is as defined above).

10. Process according to claim 9, wherein the compound of formula II, activated beforehand, is reacted with a compound of formula III at a temperature of between the ambient temperature and 200° C.

11. Process according to claim 9, wherein the preactivation of the compound of formula II includes the stages consisting in:

(i) reacting in an appropriate solvent the compound of formula II with metallic zinc in the presence of an aqueous solution of ammonium chloride at a temperature of between −10° C. and the ambient temperature;

(ii) filtering the reaction mixture to obtain a homogeneous solution of the activated compound of formula II, the said solution being employed as it is in the process according to either of claims 9 and 10.

12. Process according to claim 11, wherein the solvent in the activation stage is an ethanol/water mixture.

13. Process for the preparation of compounds of general formula I

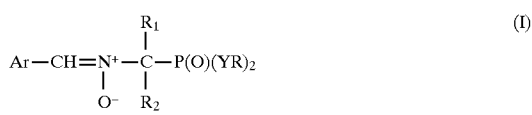

in which $R_1$ and $R_2$ independently are a $C_1$–$C_{18}$ alkyl or a phenyl group optionally substituted by $C_1$–$C_{18}$ alkyl, $C_1$–$C_{18}$ alkoxy or a halogen atom;

Y is O or $CH_2$;

R is a hydrogen atom, a $C_1$–$C_{18}$ alkyl group or a $C_6$–$C_{18}$ aryl group and, when Y is O, R can also denote an alkali metal;

Ar is an aromatic nucleus selected from a phenyl, naphthyl, 2-pyridyl, 3-pyridyl and 4-pyridyl nucleus or a benzopyridyl nucleus of formula (i)

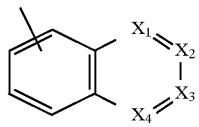
(i)

in which one of $X_1$, $X_2$, $X_3$ and $X_4$ is a nitrogen atom, the others being a carbon atom, the said aromatic nucleus being optionally C-substituted by one or more halogen atoms or one or more groups selected from $C_1$–$C_{18}$ alkyl, hydroxyl, $C_1$–$C_{18}$ alkoxy, trifluoromethyl, $C_6$–$C_{18}$ aryloxy, carboxyl, $C_1$–$C_{18}$ alkoxycarbonyl, —$SO_3M$ where M is an alkali metal or a hydrogen atom, amino optionally alkylated by one or two $C_1$–$C_{18}$ alkyl groups; and —$N^+R_3R_4R_5$ in which $R_3$, $R_4$ and $R_5$ are selected independently of one another from $C_1$–$C_{18}$ alkyl, it being understood that when the group Ar includes a quaternary nitrogen atom, it additionally includes the physiologically acceptable negative counterion necessary for electrical neutrality;

and their physiologically acceptable salts obtained by the action of an inorganic or organic base or acid, including the reaction in an appropriate solvent of a compound of formula II

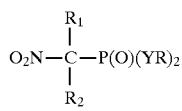
(II)

(in which $R_1$, $R_2$, Y and R are as defined above) with a compound of formula III

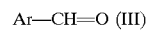
(III)

(in which Ar is as defined above)

in the presence of metallic zinc and of acetic acid.

14. Process according to claim 13, wherein the reaction takes place at a temperature of between −10° C. and the ambient temperature.

15. Cosmetic or pharmaceutical composition including as active ingredient at least one compound according to claim 1.

16. Diagnostic composition which can be employed in the evaluation of the oxidative stress, including at least one compound according to claim 1.

17. Compounds according to claim 2, wherein said halogen atom optionally substituting said aromatic nucleus is fluorine.

18. Compounds according to claim 2, wherein said M is sodium.

19. Compounds according to claim 7, wherein said carboxylate comprises an oxalate, a maleate, a citrate, a succinate or a lactate.

20. Process according to claim 10 wherein the compound of formula II, activated beforehand, is reacted with a compound of formula III at a temperature between the ambient temperature and 150° C.

* * * * *